United States Patent
Zhao (12)

(10) Patent No.: US 6,528,319 B1
(45) Date of Patent: Mar. 4, 2003

(54) METHOD FOR ANCHORING OLIGONUCLEOTIDES TO A SUBSTRATE

(75) Inventor: Xiaodong Zhao, Piscataway, NJ (US)

(73) Assignee: Amersham Biosciences Corp, Piscataway, NJ (US)

(*) Notice: Subject to any disclaimer, the term of this patent is extended or adjusted under 35 U.S.C. 154(b) by 0 days.

(21) Appl. No.: 09/388,702

(22) Filed: Sep. 2, 1999

(51) Int. Cl.[7] ............ C12Q 1/68; G01N 33/00; C12M 1/34; C07H 21/02
(52) U.S. Cl. ............ 436/94; 435/6; 435/287.1; 536/23.1
(58) Field of Search ............ 435/6, 91.1, 91.2, 435/183, 287.2; 436/94; 536/23.1, 24.3, 24.33, 25.3

(56) References Cited

U.S. PATENT DOCUMENTS

| | | |
|---|---|---|
| 5,700,637 A | 12/1997 | Southern |
| 5,770,151 A | 6/1998 | Roach et al. |
| 5,770,365 A | 6/1998 | Lane et al. |
| 5,807,522 A | 9/1998 | Brown et al. |
| 5,837,860 A | 11/1998 | Anderson et al. |
| 5,888,819 A | 3/1999 | Goelet et al. |

FOREIGN PATENT DOCUMENTS

| | | |
|---|---|---|
| WO | WO 95/00669 | 1/1995 |

OTHER PUBLICATIONS

Southern, E., et al.; Molecular Interactions on Microarrays; Nature Genetics Supplement, vol. 21, Jan. 1999, pp. 5–9.
Yang, S. and Nash, H.; Specific Photocrosslinking of DNA–Protein Complexes: Identification of Contacts Between Integration Host Factor and Its Target DNA; Proc. Natl. Acad. Sci. USA, vol. 91, Dec. 1994, pp. 12183–12187.
Fang, X., et al.; Designing a Novel Molecular Beacon for Surface–Immobilized DNA Hybridization Studies: Journal of American Chemistry Soc., 1999, 121, pp. 2921–2922.
Beattie, W., et al.; Hybridization of DNA Targets to Glass–Tethered Oligonucleotide Probes; Molecular Biotechnology, vol. 4, 1995, pp. 213–225.

*Primary Examiner*—B. L. Sisson
(74) *Attorney, Agent, or Firm*—Stephen G. Ryan; Royal N. Ronning, Jr.

(57) ABSTRACT

A method for anchoring oligonucleotides containing multiple reaction sites to a substrate. The substrate can be glass, inorganic or organic polymer, and metal. The reactive group of the substrate can contain electophilic C=C double bonds for a nucleophilic addition, or disulfide for disulfide exchange. The multiple reactive groups contained on the oligonucleotide primer can be, for example, aminoalkyl, sulfhydryl, and thiophosphate groups. The oligonucleotide primer may take the configuration of a gairpin having a loop containing multiple reactive sites. In particular, a method for attaching an oligonucleotide primer to a glass substrate is disclosed that comprises preparing a bromoacetamide derivatized silane glass surface on a glass substrate, and reacting the bromoacetamide derivatized silane glass surface with an oligonucleotide primer containing multiple thiophosphate groups to bind the oligonucleotide primer to the glass substrate. An oligonucleotide containing multiple reactive sites, as well as a probe and a kit containing the same are also disclosed.

3 Claims, 8 Drawing Sheets

2a

2b

2c

2d

METHOD FOR ANCHORING OLIGONUCLEOTIDES TO A SUBSTRATE

The instant disclosure pertains to a method for anchoring oligonucleotides containing multiple reaction sites to a substrate. In particular, the instant disclosure pertains to a method for anchoring a hairpin-shaped oligonucleotide containing a multiple site thiophosphate backbone to a glass substrate. The instant disclosure also pertains to such an oligonucleotide, as well as a probe and a kit containing the same.

BACKGROUND OF THE INVENTION

Immobilization of probe or target molecules to a solid substrate is an integral part of many bio-assay techniques. Glass substrates are generally preferred over polymer substrates for a variety of reasons. Glass substrates possess increased tolerance to higher temperatures and higher ionic strength washes. Unlike polymer substrates which are porous, nonporous glass substrates retain less extraneous material which could contribute to background signals. Furthermore, because glass is non-porous, volumes of biomolecules spotted onto the surface of a glass substrate can be kept to a minimum. Glass has low background fluorescence which does not interfere appreciably with the sensitivity of fluorescence-based detection methods. Also, the silanol surface of glass can be readily modified by the silanization of functional silanes.

In certain applications, it is preferable to covalently attach oligonucleotides and DNA samples to glass surfaces. Many of the methods presently used for covalently attaching oligonucleotides to glass surfaces employ bifimctional linkers or biotin-streptavidin linkages. For example, in *Hybridization of DNA Targets to Glass-Tethered Oligonucleotide Probes*, 4 MOLECULAR BIOTECHNOLOGY 213 (1995), Wanda G. Beattie et al. disclose the attachment of surface oligonucleotides by linking a 5' terminal amine to an epoxysilanized glass. The attachment reaction takes place in 100 mM NaOH, preferably. Small volumes (>1 nL) of reaction solution are dispensed or "spotted" onto the substrate surface and evaporate very quickly. Because the dispensed liquid evaporates so quickly, chemical reactions must be fast and efficient in order that a sufficient number of molecules attach within a brief time period. Furthermore, the alkali concentration of the reaction solution increases as the solvent evaporates, causing oligonucleotide degradation, which in turn contributes to false signals and high background in the assay. Elevated alkali concentration may also cause the silane to detach from the glass substrate.

Michael Pirrung and coworkers at Duke University have discovered that oligonucleotides with a 5'-phosphothioate react with bromoacetamide derivatized silane on a glass surface through nucleophilic substitution. The reaction takes approximately one half hour and is performed at neutral pH in aqueous solution. Unfortunately, 5'-phosphorylation is expensive, particularly for large numbers of oligomers, and any unsuccessful incorporation followed by sulfurization is not effective for attachment.

Simply increasing the concentration of probes or DNA primers to enhance the reaction rate of attachment cannot solve the dilemma of attaching oligonucleotides to surfaces. For example, the surface area of a slide is limited. The highest density of oligonucleotides on a glass surface is 0.1 pmole/$mm^2$ which is equivalent to one molecule every 39 square angstroms (Southern, et al., *Nature Genetics Supplement*, 21, 5–9 (1999)). The accessibility of oligonucleotides to the surface area (0.013 $mm^2$, 0.57 nL) of a dispensed drop in 130 $\mu$m diameter is saturated at 2.3 $\mu$M (1.33 fmole). Moreover, it is questionable whether densely packed substrates provide a solution, as densely packed substrates have been observed to reduce enzyme accessibility.

As the above discussion suggests, improvements are still possible and desirable in the area of covalent linking of oligonucleotides to surfaces, especially glass surfaces. For example, a method is needed for covalently linking oligonucleotides to glass surfaces which exhibits improved reliability and reproducibility. In particular, a method is needed which allows better control of reaction efficiency, molecular density and conformation, and enzyme compatibility. Ideally, such a method would also be economical to use. These and other concerns are addressed in greater detail below.

BRIEF SUMMARY OF THE INVENTION

The instant disclosure pertains to a method for attaching an oligonucleotide primer to a substrate that comprises attaching a reactive group onto a substrate, and reacting the substrate with an oligonucleotide primer containing multiple reactive groups corresponding to the reactive group contained on the substrate to bind the oligonucleotide primer to the glass substrate.

The substrate can be glass, inorganic or organic polymer, and metal. The reactive group of the substrate can contain electrophilic C=C double bonds for a nucleophilic addition, or disulfide for disulfide exchange. For example, the reactive group of the substrate can be maleimide and vinylsulfonate, benzene sulfonate, methanesulfonate, and trifluoromethane-sulfonate.

The multiple reactive groups contained on the oligonucleotide primer can be aminoalkyl, sulfhydryl, and thiophosphate groups. The oligonucleotide primer can contain multiple reactive groups that are the same, or it can contain at least two different reactive groups. The reactive groups contained on the oligonucleotide primer can be adjacent one another or distributed randomly throughout the primer. The oligonucleotide primer may also contain a nucleotide sequence corresponding to a protein binding site. The oligonucleotide primer may be in the configuration of a hairpin having a loop containing multiple reactive sites.

In particular, a method for attaching an oligonucleotide primer to a glass substrate is disclosed that comprises preparing a bromoacetamide derivatized silane glass surface on a glass substrate, and reacting the bromoacetamide derivatized silane glass surface with an oligonucleotide primer containing multiple thiophosphate groups to bind the oligonucleotide primer to the glass substrate.

The instant disclosure also pertains to an oligonucleotide primer comprising a backbone having multiple reactive groups for attaching said oligonucleotide primer to a substrate.

The instant disclosure also pertains to an oligonucleotide primer bound to a substrate according to the method described above.

The instant disclosure also pertains to a bioassay kit comprising an oligonucleotide primer bound to a substrate as described above.

The instant disclosure also pertains to a method for immobilizing a PCR product to a substrate that comprises creating an oligonucleotide primer by phosphorylating the 5' end of the oligonucleotide primer having multiple reaction sites and modifying the '3 end of said oligonucleotide primer to include the PCR primer sequence, hybridizing the single-stranded 3' end of said oligonucleotide primer with the PCR product, and subjecting reaction product to enzymatic or chemical ligation.

BRIEF DESCRIPTION OF THE DRAWINGS

FIG. 7A shows the image of dye terminator labeled spots of the primer extension of the ligation product of Example 2a.

DETAILED DESCRIPTION OF THE INVENTION

The instant disclosure pertains to a method for anchoring oligonucleotides containing multiple reaction sites to a substrate. The substrate may be selected from a variety of materials, including glass, inorganic or organic polymer, and metal. Preferably, the substrate is glass. Although any type of glass may be used as a substrate, the preferred substrate is borosilicate glass. The substrate may take various physical forms, such as (but not limited to) slides or beads.

The surface of the substrate is modified to facilitate attachment of the oligonucleotide to the surface. The oligonucleotide is generally modified with a nucleophile, such as aminoalkyl, sulfhydryl and thiophosphate groups. The surface of the solid support is modified with a corresponding reactive group, such as substituted benzenesulfonate, methanesulfonate, and trifluoromethanesulfonate as leaving groups for the nucleophile on the primer. The reactive groups on the solid support can also be maleimide, vinylsulfonate and acrylate as electrophilic C=C double bonds for a nucleophile, and disulfide modification for disulfide exchange. The oligonucleotide can also be modified with biotin and the surface of the substrate coated with streptavidin or avidin. Preferred reactive groups for the oligonucleotide include thiophosphate, aminoalkyl and sulfhydryl. Most preferably, the reactive groups are thiophosphate.

Multiple reactive groups on the oligonucleotide have been found to enhance reaction efficiency. Preferably, the subject oligonucleotides contain multiple groups in a single molecule capable of reacting with the surface of the substrate. In general, the oligonucleotide can contain any number of reactive groups. Preferably, the oligonucleotide contains from one to five reactive groups (see FIG. 2a which shows 5 reactive groups). The reactive groups may be arranged within one nucleoside of one another, or spaced throughout the oligonucleotide. Preferably, the reactive groups are arranged within two to six nucleosides of one another to create a hairpin structure in the oligonucleotide. The reactive groups may be the same or different. Although the subject oligonucleotides are not limited to those oligonucleotides having hairpin configurations; oligonucleotides having hair pin configurations such as those depicted in FIGS. 2c and 2d are preferred. Alternatively, the subject oligonucleotide may form a closed loop structure as shown in FIG. 2b.

Figure 1:
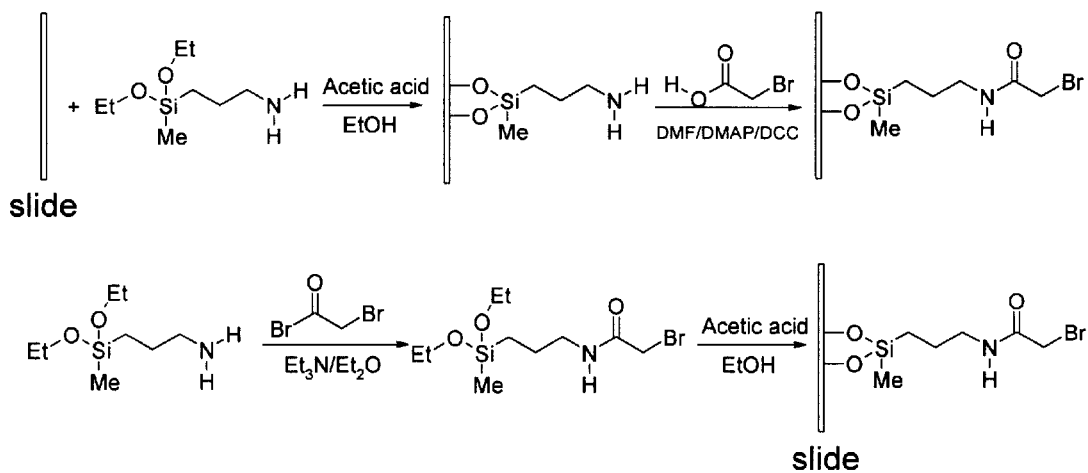
FIG. 1 shows one possible reaction scheme for preparing a bromoacetamide derivatized silane glass surface.

In a preferred embodiment, the glass substrate contains a bromoacetamide derivatized silane glass surface. FIG. 1 depicts one possible reaction scheme for preparing a bromoacetamide derivatized silane glass surface. The reactive slides can be prepared by starting from either regular glass slides or amine coated slides (commercially available from Amersham Pharmacia Biotech Inc and Corning Inc). The two-phase reaction is very efficient.

Figure 2:
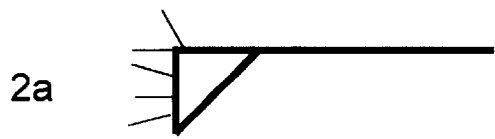
FIG. 2a shows one embodiment of the oligonucleotide primer as a tail structure having 5 groups capable of reacting with the surface of the substrate.
FIG. 2b shows one embodiment of the oligonucleotide primer having a closed loop structure.
FIG. 2c shows one embodiment of the oligonucleotide primer as a hairpin molecule containing six nucleosides connected by thiophosphates in the loop and having a single-stranded 3' end and a 5' end in the double-stranded stem.
FIG. 2d shows a detailed view of the oligonucleotide primer depicted in FIG. 2c.
Figure 2:
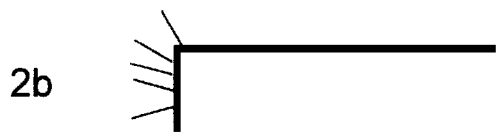
Figure 2:
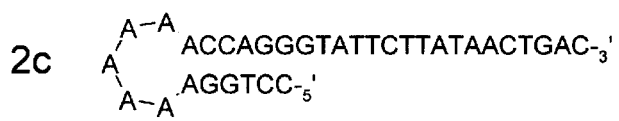
Figure 2:
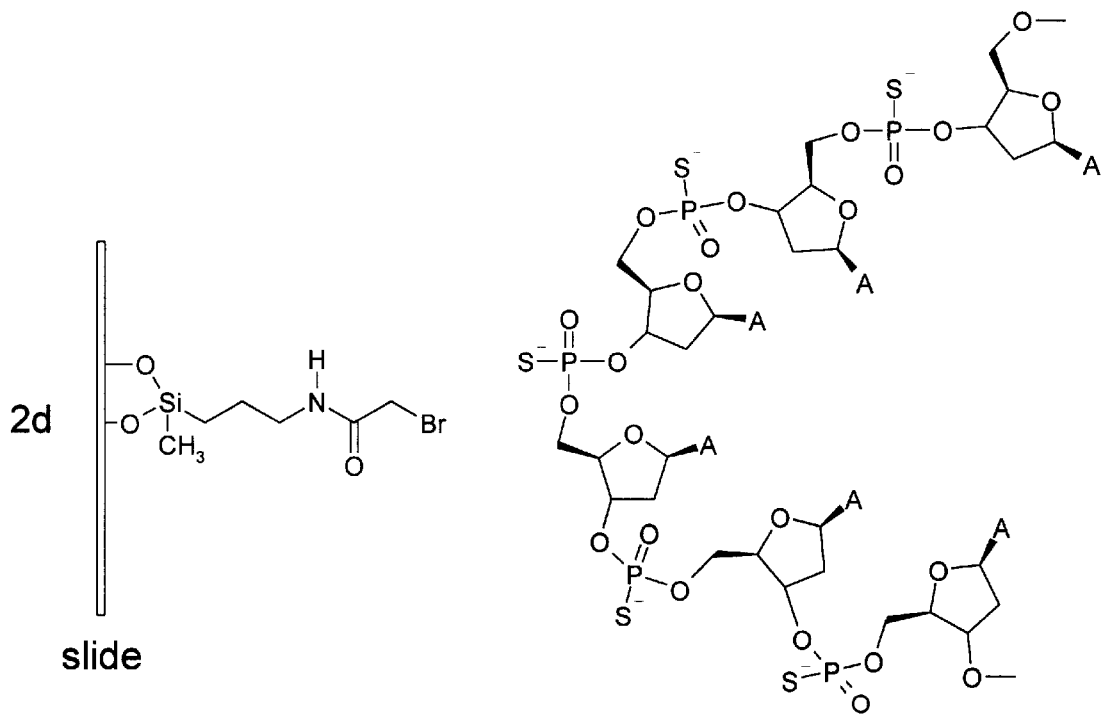
Figure 3:
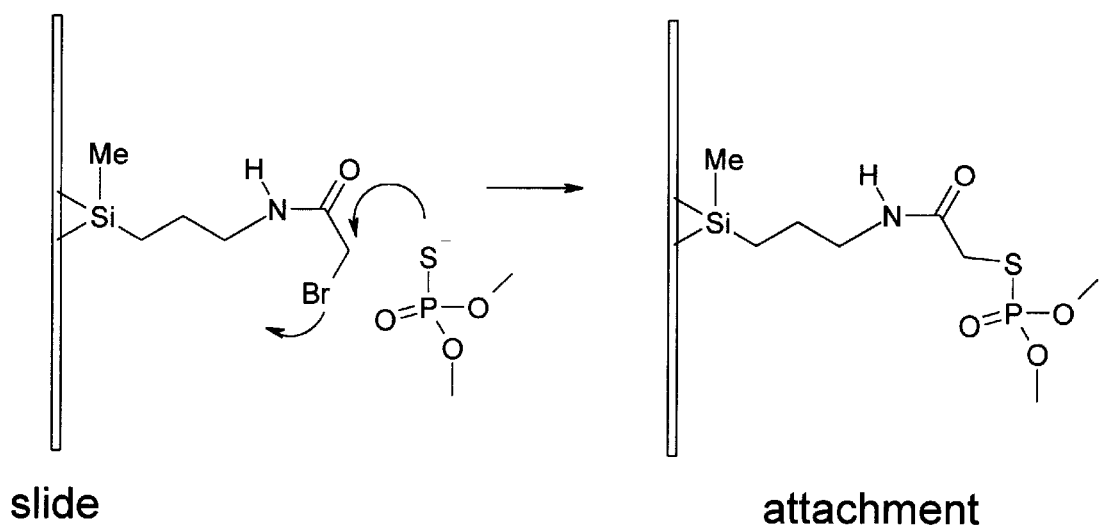
FIG. 3 shows the attachment reaction between the oligonucleotide primer depicted in FIG. 2 with the bromoacetamide derivatized silane glass surface shown in FIG. 1.
Figure 4:
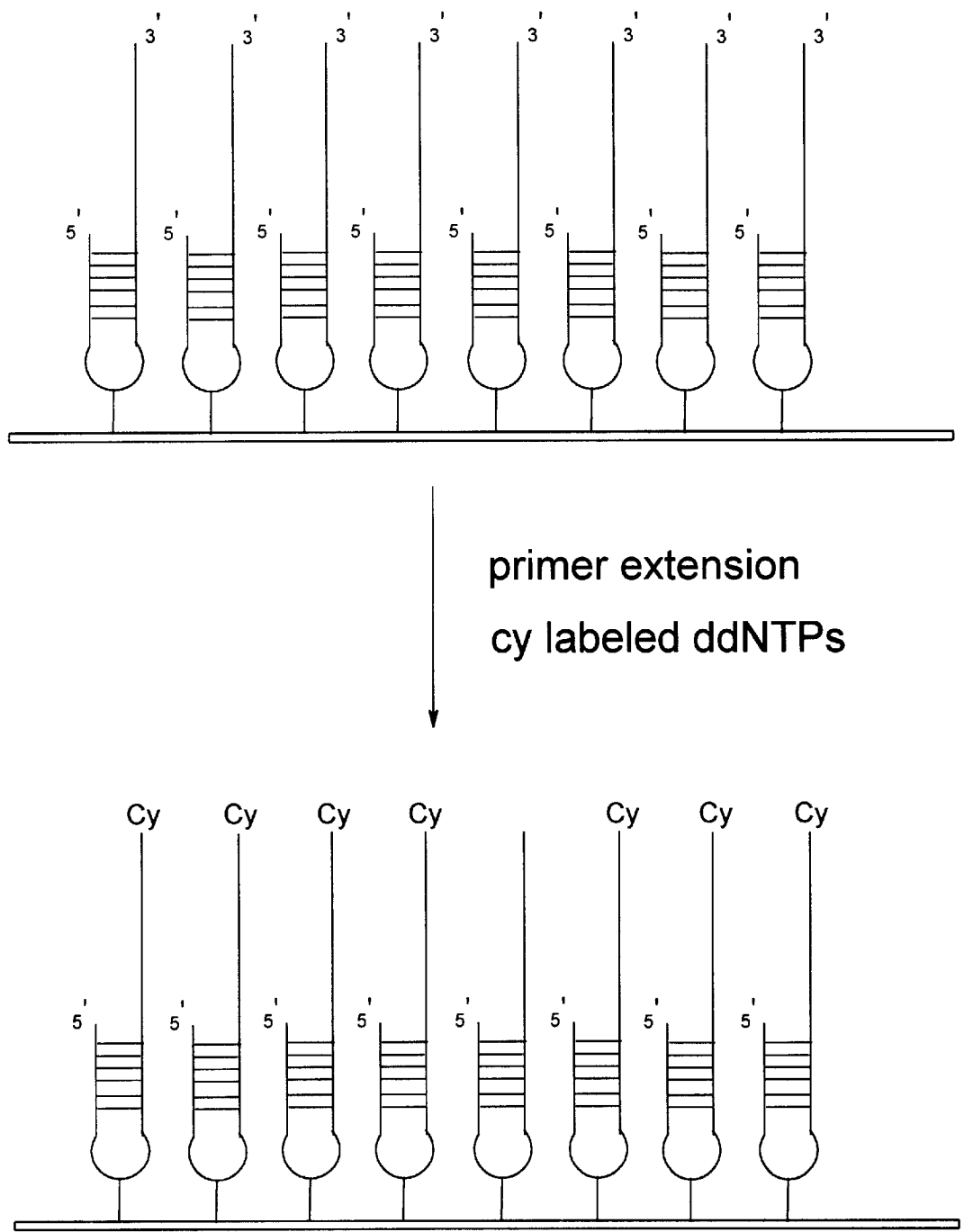
FIG. 4 shows one embodiment of an arrayed primer extension reaction involving the instant oligonucleotides.
Figure 5:
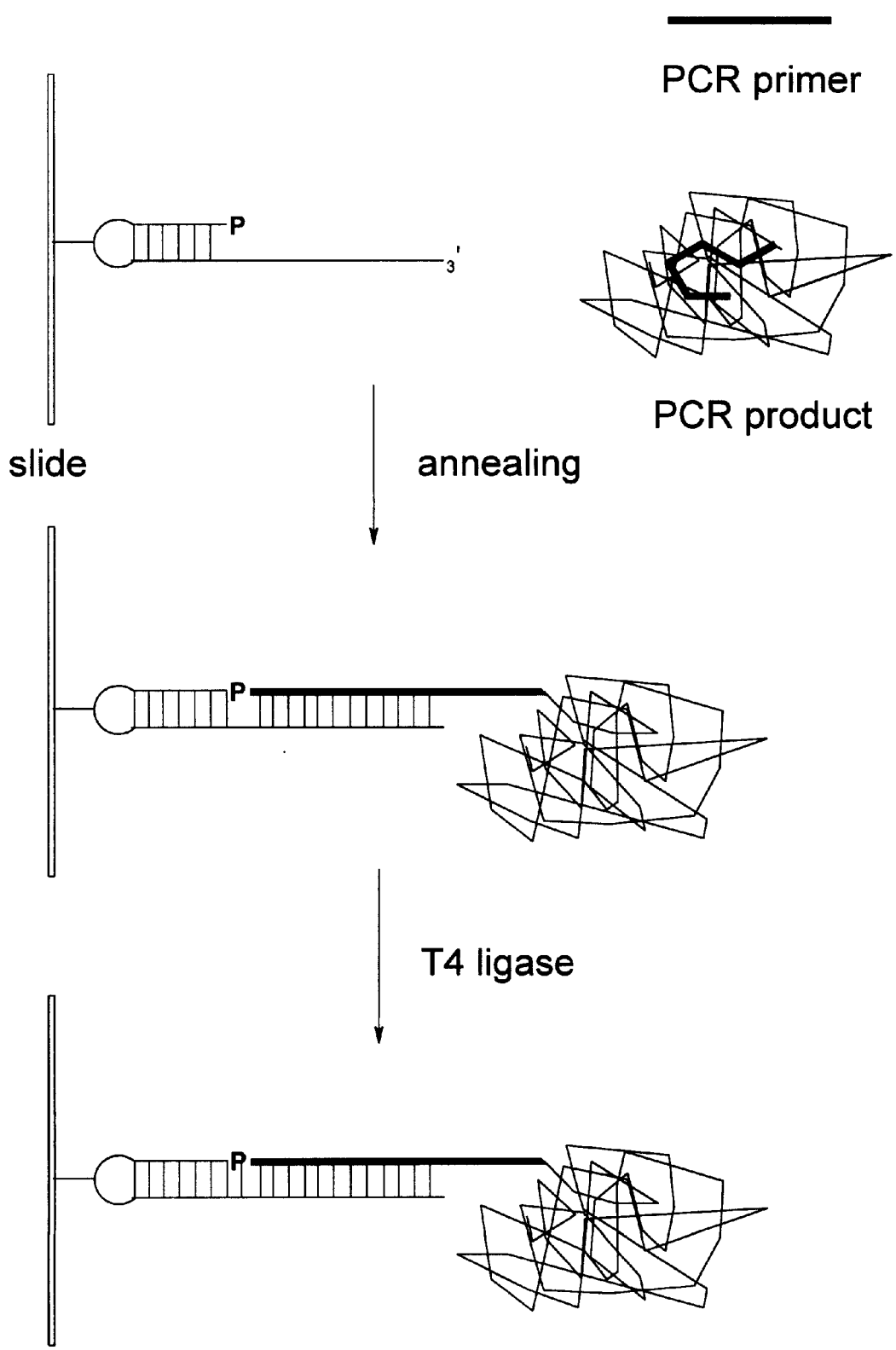
FIG. 5 shows one embodiment of a ligation reaction involving the instant oligonucleotides.

One preferred embodiment of the oligonucleotide is shown in FIG. 2c, and in greater detail in FIG. 2d. In FIGS. 2c and 2d, the oligonucleotide primer is a hairpin molecule containing six nucleosides in the loop. The nucleosides in the loop are connected by thiophosphates. The hairpin has a single-stranded 3' end and a 5' end in the double-stranded stem. The single-stranded tail is equivalent to a single-stranded oligonucleotide. This approach allows fast and efficient attachment by maintaining relatively low concentrations of oligonucleotide primers and high concentrations of reactive groups. Attachment of the primer to the bromoacetamide derivatized silane glass surface is shown in FIG. 3.

Because the oligonucleotide can attach to the substrate at any one of the reactive sites in the loop, the reaction probability (reaction rate and efficiency) increases with the number of reactive sites contained in the loop. In addition, as the anchorage of the oligonucleotide is in the backbone, both 5' and 3' ends are free for modifications with reporter groups. This is more versatile than when the anchors are at either 5' or 3' end. While a reaction occurs at one end, the other end is available for fuirther labeling. Moreover, the hairpin structure has a stem-loop moiety, which adds extra parameters to space the oligonucleotides from each other and control the density and desired upward conformation of the single-stranded moiety for primer extension as well as ligation.

This attachment scheme offers significant advantages for immobilization of cDNA or any PCR product to microchips by hybridization and ligation. For example, if the 5' end of the hairpin is phosphorylated chemically during synthesis and the 3' single-stranded tail has a sequence which is complementary to a PCR primer sequence, the PCR product could hybridize with the single-stranded tail and be linked covalently by enzymatic or chemical ligation. Many of the current approaches for covalently attaching a PCR product to a surface focus mainly on modifying PCR primers. One disadvantage of this approach is that the reactive position may be buried in the self-folded macromolecule. The approach of hybridization followed by ligation may have a higher reaction probability than the simple interaction of reactive groups, since such bimolecular reaction depends on more factors than the sole collision probability of two substrates. The instant method and oligonucleotides are not limited to the hybridization of nucleic acids. For example, the oligonucleotide primer may also contain a nucleotide sequence corresponding to a protein binding site and would be useful, for example, in protein assays.

The instant attachment method has the potential to immobilize oligonucleotides and DNAs by a covalent bond to a silica based glass surface with improved control of reaction efficiency, molecular density and conformation, and enzyme compatibility. Given the versatility of the instant oligonucleotides, it is possible that uses may be found with substrates other than those mentioned. The following examples are for illustration purposes only and should not be used in any way to limit the appended claims.

EXAMPLES

Slide Preparation

Pre-washed glass slides (25×75 mm microscope slides from VWR Scientific Products West Chester, Pa.) were immersed for 3 minutes in 95% ethanol (350 mL) containing approximately 2–3% (wt/vol) 3-aminopropylmethylethoxysilane, pH 5.0, washed with ethanol, and cured in an oven at 75° C. for 4 hours. After curing, the glass slides were placed on a glass rack and immersed in 160 mL of N, N-dimethylformamide (DMF) containing bromoacetic acid (2.0 g, 14.9 mmol), 4-(dimethylamino)-pyridine (DMAP) (0.4 g, 3.3 mmol), and 1,3-dicyclohexylcarbodiimide (DCC) (4.0 g, 19.4 mmol). The reaction container was placed on a shaker in the dark for 4 hours. The slides were then washed with ethanol and air-dried.

The hairpin oligonucleotide has five thiophosphates in the six nucleoside loop with a stem of five base pairs and a single stranded arm of seventeen bases which is commercially available from Genosys (The Woodland Texas). The thiophosphates are located to the right of lower case a's in the sequence of CCTGGaaaaaACCAGGGTATTCTTATAACTGAC<SEQ. ID NO. 1>. The hairpin oligonucleotide was dissolved and stored in 1×TE (10 mM Tris-HCl, 1 mM EDTA, pH 7.0). The concentration of oligonucleotide was calculated based on spectrophotometric measurement. The oligonucleotide (100 to 0.4 µM in a dilution series) was spotted on a bromoacetamide silane coated glass surface using a Molecular Dynamics Gen III spotter (Molecular Dynamics, Sunnyvale, Calif.). The volume of the spots was 0.7 nL and the size was 130 µm in diameter.

Example 1

Primer Extension

Example 1a

Figure 6:
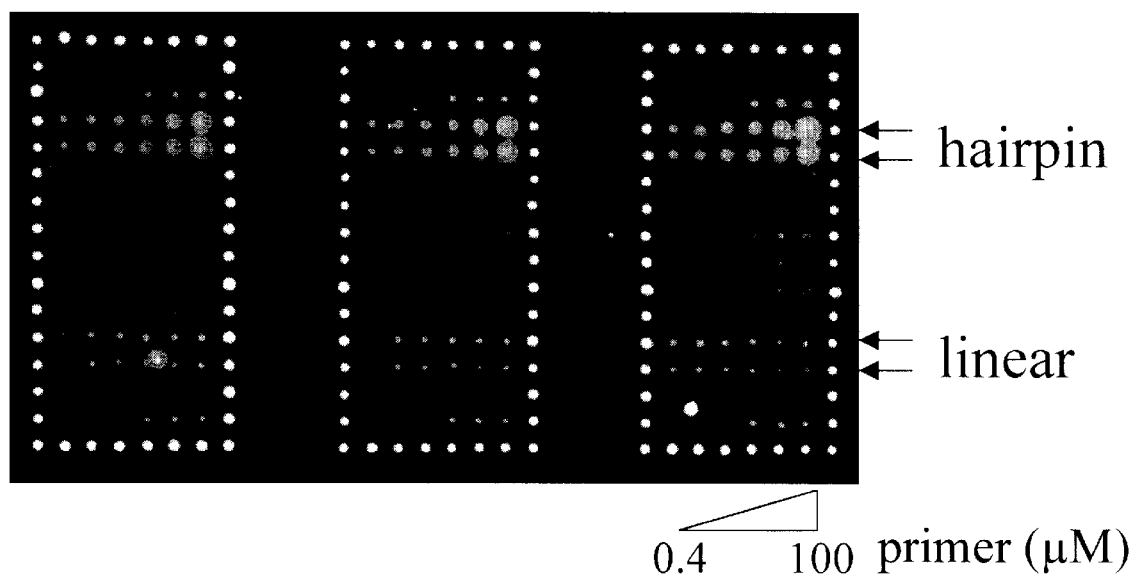
FIG. 6 shows the image of dye terminator labeled spots of both linear and hairpin oligonucleotide primer extension reactions conducted in Example 1

The slide with primers was placed on a hot plate heated to 48° C. Primer extension was carried out in 45 µL of Thermo Sequenase buffer (25 mM TAPS buffer, pH 9.3, 50 mM KCl, 2 mM MgCl$_2$, 1 mM 2-mercaptoethanol) with 0.5 µM of dye terminator Cy5-ddGTP, Thermo Sequenase DNA polymerase (4 unit). The templates used were 2 pmol of either a 23-mer CTGATCGTCAGTTATAAGAATAC<SEQ. ID NO. 2>, or a 28-mer CTGATCGTCAGTTATAAGAATACTAGCA<SEO. ID NO. 3> (giving a branched structure at 5' end of the hairpin stem). The reaction mixture was washed away with boiling water after being incubated for 10 minutes. The image of the dye terminator labeled spots was obtained using a Avalanche microscanner (Molecular Dynamics, Sunnyvale, Calif.). As shown in FIG. 6, the integral of the fluorescence intensity of each spot was observed to vary linearly with the concentration of the spotted solution.

Example 1b

Figure 8A:
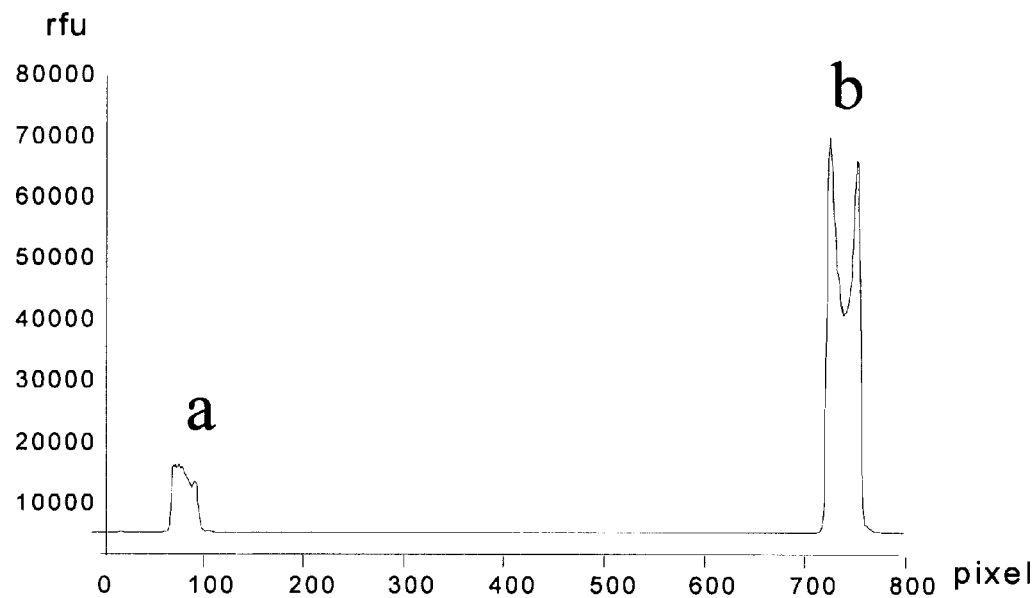
FIG. 8A shows a comparison of an oligonucleotide having one reactive site (Peak a) with an oligonucleotide having five reactive sites (Peak b). As shown by the intensity of the label, Peak b has approximately 5 times the incorporated fluorescence label than Peak a which has only one reactive site.
Figure 8B:
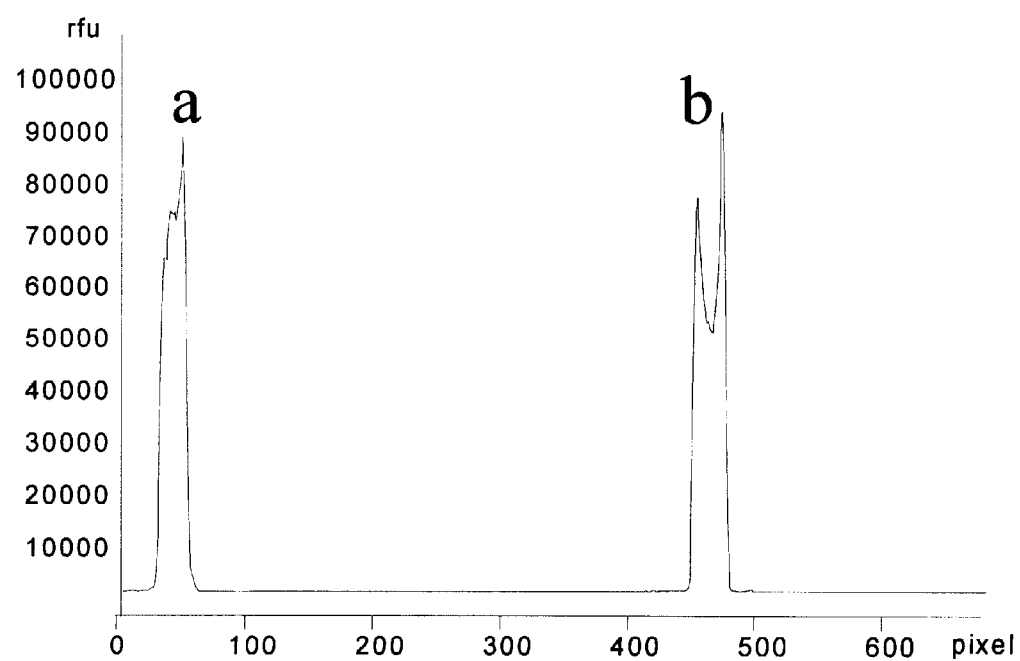
FIG. 8B shows that an oligonucleotide having five reactive sites near the tail position (Peak a) has approximately the same incorporated fluorescence label as a hairpin oligonucleotide having five reactive sites (Peak b).

Four oligonucleotides modified differently with thiophosphates in the backbone were purchased from Operon Technologies, Inc (Alameda, Calif.). The thiophosphates are located to the right of lower case a's in the following sequences: CCTGGaaACCAGGGTATTCTTATAACTGAC<SEQ. ID NO. 4> has two thiophosphates in the haipin-loop. AaaaaACCAGGGTATTCTTATAACTGAC<SEQ. ID NO. 5> has five thiophosphates in the 5' tail. AAaCCAGGGTATTCTTATAACTGAC<SEQ. ID NO. 6> and aAACCAGGGTATTCTTATAACTGAC<SEQ. ID NO. 7>. The oligonucleotide was dissolved and stored in 1×TE buffer. The concentration of oligonucleotide was calculated based on spectrophotometric measurement. The primers were spotted from 50 iM solution. Primer extension was carried out similarly in 45 µL of Thermo Sequenase buffer. The templates used were 2 pmol of the 23-mer CTGATCGTCAGTTATAAGAATAC<SEQ. ID NO. 8>. The signal intensity of the incorporated Cy5-ddGTP changed dramatically with the number of thiophosphates in the primers. As shown in FIGS. 8A, the signal had a five fold difference in the primers with either one (Peak a) or five thiophosphates (Peak b). FIG. 8B shows that an oligonucleotide having five reactive sites near the tail position (Peak a) has approximately the same incorporated fluorescence label as a hairpin oligonucleotide having five reactive sites.

Example 2

Ligation

Example 2a

Figure 7A:
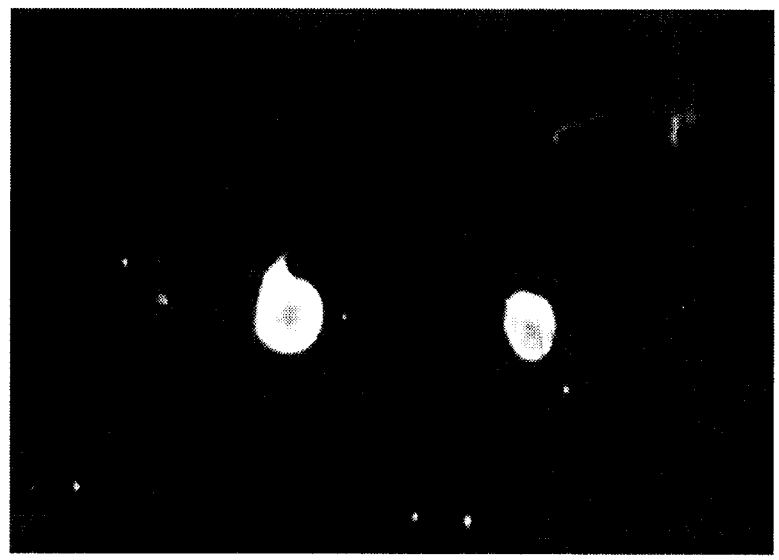

A 50-mer thiophosphate hairpin, pGAATTCTACCCTG-GaaaaaaCCAGGGTAGAATTCGTAAAACGACGGCCAG <SEQ. ID NO, 9>, was phosphorylated chemically during synthesis and immobilized to a glass surface as described previously. The ligation is performed in 40 µL of enzyme buffer (66 mM Tris-HCl, pH 7.6, 6.6 mM MgCl$_2$, 10 mM DTT, 66 µM ATP) containing 3 units of T4 DNA ligase and 200 pmol of a ligation fragment, 3'-CATTTTGCTGCCGGTCACGGTTC-5'<SEQ. ID NO. 10>. The reaction was incubated at room temperature for 2 hours and washed with hot water. A primer extension was then performed with Cy5-ddTTP. The ligation product served as a self-extension primer to be labeled with Cy5-ddTTP by thermal sequenase. See FIG. 7a.

Example 2b

Figure 7B:
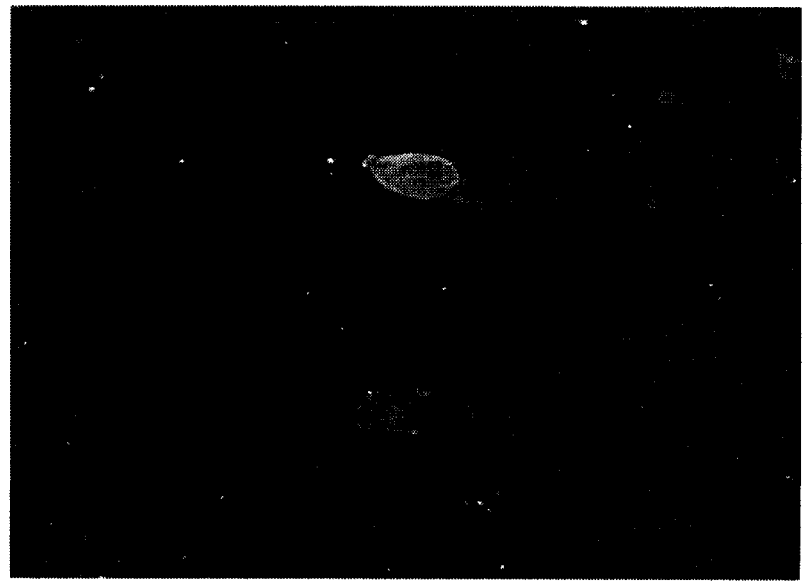
FIG. 7B shows the image of dye terminator labeled spots of the primer extension of the ligation product of Example 2b.

The ligation of a 100-mer PCR product of pUC-18 was performed with thermal stable Pfu DNA ligase at 48° C. The reaction mixture contained 40 AL of enzyme buffer (20 mM Tris-HCl, pH 7.5, 20 mM KCl, 10 mM MgCl$_2$, 1 mM DTT, 10 µM ATP, 0.1% lgepal) and 4 units of Pfu DNA ligase and a 100-mer fragment (5 pmole) of pUC-18, which was amplified by universal and reverse M13 primers. The reaction was incubated at 48° C. for 15 min and then washed with sufficient hot water to remove excess reaction components. A primer extension was then performed with Cy3-ddTTP. The ligation product serves as a self-extension primer to be labeled with Cy3-ddTTP by thermal sequenase to confirm the ligation. See FIG. 7b.

Although various embodiments of the instant invention are described in detail above, the instant invention is not limited to such specific examples. Various modifications will be readily apparent to one of ordinary skill in the art and fall within the spirit and scope of the following appended claims.

What is claimed is:

1. A method for attaching an oligonucleotide primer to a glass substrate that comprises:
   A) preparing a bromoacetamide derivatized silane glass surface on a glass substrate, and
   B) reacting an oligonucleotide primer containing multiple thiophosphate groups with the bromoacetamide derivatized silane glass surface of A) to bind the oligonucleotide primer to the glass substrate.

2. The method according to claim 1, wherein the multiple thiophosphate groups contained on the oligonucleotide primer are adjacent one another.

3. The method of claim 1, wherein said oligonucleotide primer is in the configuration of a hairpin having a loop containing said multiple thiophosphate groups.

* * * * *

```
                        SEQUENCE LISTING

<160> NUMBER OF SEQ ID NOS: 10

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
cctggaaaaa accagggtat tcttataact gac                                   33

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
ctgatcgtca gttataagaa tac                                              23

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
ctgatcgtca gttataagaa tactagca                                         28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
cctggaaacc agggtattct tataactgac                                       30

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
aaaaaaccag ggtattctta taactgac                                         28
```

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
aaaccagggt attcttataa ctgac                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
aaaccagggt attcttataa ctgac                                              25

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
ctgatcgtca gttataagaa tac                                                23

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
gaattctacc ctggaaaaaa ccagggtaga attcgtaaaa cgacggccag                   50

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
cattttgctg ccggtcacgg ttc                                                23
```